United States Patent [19]
Alexander et al.

[11] Patent Number: 5,834,182
[45] Date of Patent: *Nov. 10, 1998

[54] METHOD FOR INCREASING TRANSDUCTION OF CELLS BY ADENO-ASSOCIATED VIRUS VECTORS

[75] Inventors: Ian E. Alexander, Middle Dural, Australia; David W. Russell; A. Dusty Miller, both of Seattle, Wash.

[73] Assignee: Fred Hutchinson Cancer Research Center

[*] Notice: The term of this patent shall not extend beyond the expiration date of Pat. No. 5,604,090.

[21] Appl. No.: 750,274

[22] PCT Filed: Jun. 5, 1995

[86] PCT No.: PCT/US95/07202

§ 371 Date: Feb. 25, 1997

§ 102(e) Date: Feb. 25, 1997

[87] PCT Pub. No.: WO95/33824

PCT Pub. Date: Dec. 14, 1995

Related U.S. Application Data

[63] Continuation-in-part of Ser. No. 254,312, Jun. 6, 1994, Pat. No. 5,604,090.

[51] Int. Cl.⁶ .............................. C12N 15/87; C12N 5/00; C12N 15/86; C12Q 1/70
[52] U.S. Cl. ................................. 435/5; 424/93.2; 435/6; 435/172.3
[58] Field of Search ................................. 435/6, 5, 172.3, 435/320.1, 29, 70.1; 424/93.2, 240.2

[56] References Cited

U.S. PATENT DOCUMENTS 5,604,090  2/1997  Alexander ................................. 435/5

OTHER PUBLICATIONS

Orkin et al. "Report & Recommendations of the Panel to Assess the NIH Inventor in Research on Gene Therapy", 1995.
Miller et al., "Gene transfer by retrovirus vectors occurs only in cells that are actively replicating at the time of infection," *Mol. Cell. Biol.* 10:4239–4242 (1990).
Grunhaus et al., "Adenoviruses as cloning vectors," *Seminars in Virology* 3:237–252 (1992).
Geller et al., "Infection of cultured central nervous system neurons with a defective herpes simplex virus 1 vector results in stable expression of *Excherichia coli* β–galactosidase," *Proc. Natl. Acad. Sci. USA* 87:1149–1153 (1990).
Hermonat et al., "Use of adeno–associated virus as a mammalian DNA cloning vector: transduction of neomycin resistance into mammalian tissue culture cells," *Proc. Natl. Acad. Sci. USA* 81:6466–6470 (1984).
Lebkowski et al., "Adeno–associated virus: a vector system for efficient introduction and integration of DNA into a variety of mammalian cell types," *Mol. Cell. Biol.* 8:3988–3996 (1988).

McLaughlin et al., "Adeno–associated virus general transduction vectors: analysis of provinral structures," *J. Virol.* 62:1963–1973 (1988).
Samulski et al., "Helper–free stocks of recombinant adeno–associated viruses: normal integration does not require viral gene expression," *J. Virol.* 63:3822–3828 (1989).
Carter, "Adeno–associated virus vectors," *Curr. Opin. Biotech.* 3:533–539 (1992).
Muzcyzka, "Use of adeno–associated virus as a general transduction vector for mammalian cells," *Curr. Top. Microbiol. Immunol.* 158:97–129 (1992).
Flotte et al., "Gene expression from adeno–associated virus vectors in airway epithelial cells," *Am. J. Respir. Cell Mol. Biol.* 7:349–356 (1992a).
Egan et al., "Defective regulation of outwardly rectifying Cl– channels by protein kinase A corrected by insertion of CFTR," *Nature* 358:581–584 (1992).
Flotte et al., "Expression of the cystic fibrosis transmembrane conductance regulator from a novel adeno–associated virus promoter," *J. Biol. Chem.* 268:3781–3790 (1993a).
Walsh et al., "Regulated high level expression of a human γ–globin gene introduced into erythroid cells by an adeno–associated virus vector," *Proc. Natl. Acad. Sci. USA* 89:7257–7261 (1992).
Flotte et al., "Stable in vivo expression of the cystic fibrosis transmembrane conductance regulator with an adeno–associated virus vector," *Proc. Natl. Acad. Sci. USA* 90:10613–10617 (1993).
Sambrook et al., *Molecular Cloning*, Cold Spring Harbor, New York (1989).
Gey et al., "Tissue culture studies of the proliferative capacity of cervical carcinoma and normal epithelium," *Cancer Res.* 12:264–265 (1952).
Graham et al., "Characteristics of a human cell line transformed by DNA from human adenovirus type 5," *J. Gen. Virol.* 36:59–72 (1977).
Limon et al., "Application of long–term collagenase disaggregation for the cytogenetic analysis of human solid tumors," *Cancer Genet. Cytogenet.* 23:305–313 (1986).

(List continued on next page.)

*Primary Examiner*—Nancy Degen
*Attorney, Agent, or Firm*—Christensen, O'Connor, Johnson & Kindness PLLC

[57] ABSTRACT

This invention includes methods for increasing the efficiency of transduction of cells, including non-dividing cells, by recombinant AAV vectors. The methods utilize agents that alter certain aspects of DNA metabolism, more specifically, that affect DNA synthesis and/or affect repair, that impact on maintenance of chromosomal integrity, and/ or that cause damage to the cellular DNA. Agents and vectors can now also be preselected and screened for transducing ability and/or transducing agents for their effect on DNA metabolism. These agents include tritiated nucleotides such as thymidine, gamma irradiation, UV irradiation, cis-platinum, etoposide, hydroxyurea and aphidicolin.

9 Claims, No Drawings

OTHER PUBLICATIONS

Palmer et al., "Efficient retrovirus–mediated transfer and expression of a human adenosine deaminase gene in diploid skin fibroblasts from an adenosine deaminase–deficient human," *Proc. Natl. Sci. USA* 84:1055–1059 (1987).

Samulski et al., "Cloning of adeno–associated virus into pBR322: rescue of intact virus from the recombinant plasmid in human cells," *Proc. Natl. Acad. Sci. USA* 79:2077–2081 (1982).

Weiss et al., eds., *RNA Tumor Viruses*, Cold Spring Harbor Laboratory Press, Cold Spring Harbor, New York, 2nd ed., p. 766 (1985).

Kam et al., "Cloning, sequencing, and chromosomal localization of human term placental alkaline phosphatase cDNA," *Proc. Natl. Acad. Sci. USA* 82:8715–8719 (1985).

Reddy et al., "The genome of simian virus 40," *Science* 200:494–502 (1978).

Beck et al., "Nucleotide sequence and exact localization of the neomycin phosphotransferase gene from transposon Tn5," *Gene* 19:327–336 (1982).

Boissy et al., "An *Eschericia coli recBCsbcBrecF* host permits the deletion–resistant propagation of plasmid clones containing the 5'–terminal palindrome of minute virus of mice." *Gene* 35:179–185 (1985).

Ruffing et al., "Assembly of viruslike particles by recombinant structural proteins of adeno–associated virus type 2 in insect cells," *J. Virol.* 66:6922–6930 (1992).

Yakobson et al., "Replication of adeno–associated virus in synchronized cells without the addition of a helper virus," *J. Virol.* 61:972–981 (1987).

Miller et al., "Cloning of the cellular receptor for amphotropic murine retroviruses reveals homology to that for gibbon ape leukemia virus," *Proc. Natl. Acad. Sci. USA* 91:78–82 (1994).

Miller et al., "Improved retroviral vectors for gene transfer and expression," *Biotechniques* 7:980–990 (1989).

Friedrich et al., "Promoter traps in embryonic stem cells: a genetic screen to identify and mutate developmental genes in mice," *Genes and Development* 5:1513–1523 (1991).

Fields–Berry et al., "A recombinant retrovirus encoding alkaline phosphatase confirms clonal boundry assignment in lineage analysis of murine retina," *Proc. Natl. Sci. USA* 89:693–697 (1992).

Berger et al., "Expression of active, membrane bound human placental alkaline phosphatase by transfected simian cells," *Proc. Natl. Acad. Sci. USA* 84:4885–4889 (1987).

Berger et al., "Secreted placental alkaline phosphatase: a powerful new quantitative indicator of gene expression in eukaryotic cells," *Gene* 66:1–10 (1988).

Bradford, "A rapid and sensitive method for quantitation of microgram quantities of protein utilizing the principle of protein–dye binding," *Anal. Biochem.* 72:248–254 (1976).

Hirt, "Selective extraction of polyoma DNA from infected mouse cell cultures," *J. Mol. Biol.* 26:365–369 (1967).

Yalkinoglu et al., "DNA amplification of adeno–associated virus as a response to cellular genotoxic stress," *Cancer Res.* 48:3124–3129 (1988).

Flickinger, J.C. et al., "A Multi–Institutional Experience With Stereotactic Radiosurgery For Solitary Brain Metastasis," *Int. J. Radiation Oncology Biol. Phys.* 28(4):797–802 (1994).

Russell, D.W. et al., "DNA synthesis and topoisomerase inhibitors increase transduction by adeno–associated virus vectors," *Proc. Natl. Acad. Sci. USA*, 92:5719–5723 (1995).

Alexander, I.E. et al., "DNA Damaging Agents Greatly Increase the Transduction of Nondividing Cells by Adeno–Associated Virus Vectors," *J. Virology*, 68(12):8282–8287 (1994).

METHOD FOR INCREASING TRANSDUCTION OF CELLS BY ADENO-ASSOCIATED VIRUS VECTORS

This application is the U.S. national stage application of International application Ser. No. PCT/US95/07202, filed Jun. 5, 1995, published as WO95/33824 Dec. 14, 1995, which was a continuation-in-part of U.S. application Ser. No. 08/254,312, filed Jun. 6, 1994, now U.S. Pat. No. 5,604,090 and claims the benefit of the filing dates thereof under 35 U.S.C. § 120.

GOVERNMENT SUPPORT

This invention was made, in part, with government support from the National Institutes of Health under Grant Nos. HL 41212 and HL 36444. The United States Government has certain rights in this invention.

FIELD OF THE INVENTION

This invention relates generally to adeno-associated virus (AAV) vectors for gene transfer and, more specifically, to methods for increasing transduction of cells with recombinant adeno-associated virus (AAV) vectors.

BACKGROUND OF THE INVENTION

The efficient delivery of therapeutic genes to non-dividing cells with resultant long-term stable expression remains a major goal in the development of gene therapy. None of the currently available vector systems has been shown to be capable of both efficient transduction of non-dividing cells and long-term expression through stable integration of the vector genome into host cell DNA. Retroviral vectors based on Moloney murine leukemia virus, while capable of integration and stable long-term expression, require cell division for efficient transduction. Miller D. G. et al., *Mol. Cell. Biol* 10, 4239–4242 (1990). In contrast, vectors based on adenovirus and herpes simplex virus are capable of transducing non-dividing cells but do not integrate into host cell DNA with any appreciable frequency. See Grunhaus A. et al., *Seminars in Virol* 3, 237–252 (1992); Geller A. I. et al., *Proc. Natl Acad Sci U.S.A.* 87, 1149–1153 (1990). The less well characterized vectors based on the dependent parvovirus, adeno-associated virus (AAV), have been shown to integrate, but their potential for transducing non-dividing cells has yet to be fully investigated. See Hermonat P. L. et al., *Proc. Natl. Acad Sci. U.S.A.* 81, 6466–6470 (1984); Lebrowski J. S. et al., *Mol. Cell. Biol.* 8, 3988–3996 (1988); McLaughlin S. K. et al., *J Virol.* 62, 1963–1973 (1988); and Samulski R. J. et al., *J Virol.* 63, 3822–3828 (1989).

Adeno-associated virus (AAV) vectors are among a small number of recombinant virus vector systems which have been shown to have utility as both in vitro and in vivo gene transfer vectors (reviewed in Carter, 1992, *Curr. Opinion Biotech.* 3, 533–539 (1992); Muzcyzka, *Curr. Top. Microbiol. Immunol.* 158, 97–129) (1992) and thus are potentially of great importance for human gene therapy. AAV vectors are capable of stable DNA integration and expression in a variety of cells including cystic fibrosis (CF) bronchial and nasal epithelial cells (Flotte et al., *Am. J Respir. Cell Mol Biol.* 7, 349–356 (1992a)); Egan et al., *Nature*, 358, 581–584 (1992); Flotte et al., *J Biol. Chem.* 268, 3781–3790 (1993a); human bone marrow-derived erythroleukemia cells (Walsh et al., *Proc. Natl. Acad Sci. US.A.* 89, 7257–7261 (1992)), and several others. See also Flotte et al., *Proc. Natl. Acad Sci. U.S.A.,* 90, 10613–10617 (1993).

We have recently demonstrated that AAV vectors preferentially transduce cells in S phase of the cell cycle. However, transduction events do occur independent of S phase at low frequency. The factors within a S phase cell that facilitate transduction by AAV vectors remain undefined, but are likely to directly involve or be closely linked to DNA synthesis. Possible factors include host cell polymerases required for the conversion of the single-stranded input genomes to double-stranded molecules and/or cellular factors facilitating vector integration.

SUMMARY OF THE INVENTION

Of the viral vector systems currently available for gene transfer applications, none has been demonstrated to be capable of both efficient transduction of non-dividing cells and long-term expression through stable integration into host cell DNA. We have discovered that the transduction efficiency on non-dividing cells of the integrating vector system based on adeno-associated virus (AAV) can be greatly increased by treatment with agents which affect DNA metabolism. Increased transduction, particularly of non-dividing cells, can facilitate gene transfer and is useful in many applications, including the manufacture of gene products and therapeutic applications. In addition, we have discovered that the transduction efficiency of both dividing and non-dividing cells with recombinant AAV is increased by treatment with agents that alter certain aspects of DNA metabolism, more specifically, that alter DNA synthesis, DNA repair, and/or maintenance of chromosomal and DNA strand integrity. Thus, the invention includes methods for increasing the efficiency of transduction of cells, including non-dividing cells, by recombinant AAV vectors by treatment with agents that alter DNA metabolism. Accordingly, embodiments of the invention include the following.

A method of increasing AAV transduction of a cell comprising the steps of:
  a. providing an agent that alters DNA metabolism in a cell;
  b. treating the cell with an effective level of the agent;
  c. providing a recombinant AAV vector capable of integrating into DNA within the cell; and
  d. incubating the AAV vector with the cell to allow transduction of the cell by the AAV vector.

A method of increasing AAV transduction of a cell comprising the steps of:
  a. providing an agent that causes damage to cellular DNA;
  b. treating the cell with an effective level of the damaging agent;
  c. providing a recombinant AAV vector capable of integrating into the cell; and
  d. incubating the AAV vector with the cell to allow transduction of the cell by the AAV vector.

A method of increasing AAV transduction of a cell comprising the steps of:
  a. providing an agent that interferes with cellular DNA synthesis;
  b. treating the cell with an effective level of the agent;
  c. providing a recombinant AAV vector capable of integrating into DNA within the cell; and
  d. incubating the AAV vector with the cell to allow transduction of the cell with the AAV vector.

A method of increasing AAV transduction of a cell comprising the steps of:
  a. providing an agent which disrupts chromosomal integrity;
  b. treating the cell with an effective level of the agent;
  c. providing a recombinant AAV vector capable of integrating into DNA within the cell; and d. incubating the AAV vector with the cell to allow transduction of the cell with the AAV vector.

A method of screening for a transduction-increasing agent of a cell population comprising the steps of:
a. preselecting an agent that alters DNA metabolism;
b. providing the agent;
c. treating the cell population with the agent at a level sufficient to alter DNA metabolism;
d. providing a recombinant AAV vector capable of integrating into DNA within the cell population;
e. incubating the AAV vector with the cell population to allow transduction of the cell population with the AAV vector; and
f. assaying for the level of transduction of the cell population.

DETAILED DESCRIPTION OF THE PREFERRED EMBODIMENT

The methods of the invention, unless otherwise indicated, utilize techniques known to those in the fields of cell biology, molecular biology and gene transfer. Methods such as these are published in, for example, Muzyczka N., *Curr. Topics Microbiol Immunol.* 158, 97–129 (1992) and Sambrook J. et al., *Molecular Cloning,* Cold Spring Harbor Laboratory Press, Cold Spring Harbor, N.Y. (1989).

Terms used herein are defined as follows:

The term "DNA metabolism" refers to cellular mechanisms involved in DNA repair, DNA synthesis, and/or maintenance of chromosomal and DNA strand integrity.

The term "agent altering DNA metabolism" refers to an agent that alters cellular DNA metabolism, and includes agents which cause structural DNA damage and/or loss of chromosomal integrity at the molecular, macromolecular, strand and chromosomal levels, those which alter DNA repair, and/or those which alter DNA synthesis.

The term "non-dividing cell" refers to a cell not passing through the cell cycle, specifically not the S or M phases.

The term "stationary culture" refers to conditions of cell culture under which only a minimal percentage of the cells, e.g. generally about 4%, are undergoing replication.

The term "recombinant AAV vector" refers to a vector derived from AAV that is capable of insertion into DNA, and that contains a heterologous sequence of polynucleotides operably linked to one or more control sequences that allow its transcription.

The term "transduction" refers to the viral transfer of genetic material and its expression in a recipient cell.

The term "effective level" of agent refers to an amount or dosage of agent which, used in accord with other methods of the invention, causes an increase in transduction of a cell or cell population over a nontreated cell or cell population transduced under similar conditions (i.e. over control levels). Generally speaking, this will be a level which alters DNA metabolism as herein defined.

The term "equivalent analog" of an agent refers to an agent which has the same or similar mechanisms of action on DNA metabolism as the agent to which it is an analog, and which causes an increase in transduction by AAV vectors. In the case of chemical agents, this would include structural analogs which have the same or similar effects on DNA metabolism as herein defined. Equivalent analogs also include various forms of radiation having mechanisms of action similar to ultraviolet and gamma radiation.

The present invention provides methods for increasing transduction of cells, including non-dividing cells, by AAV recombinant vectors through treatment of the cells with agents that alter various aspects of DNA metabolism. Treatment with these agents can result in actual structural damage to the DNA, the induction of cellular DNA repair, interference with DNA synthesis and/or disruption of chromosomal integrity in the cell. It will also be appreciated that agents which alter DNA metabolism as defined herein include those whose principal mechanism or modes of action are directed to DNA metabolism, not those whose effect is remote.

In the practice of the methods of the invention, a cell or cell population is treated with an effective level of agent and exposed to AAV vector capable of integration into cellular DNA under conditions allowing transduction. The agent is, as previously defined, an agent which alters DNA metabolism, i.e. alters DNA strand integrity, DNA repair, DNA synthesis and/or chromosomal integrity and any combination of the above. It will be appreciated that treatment by the agent can occur concurrently with pre- or post-exposure to AAV vector or in combinations thereof. It will also be appreciated that the treatment with the agent can comprise a series of treatments at various intervals, also occurring pre-, post- or during exposure to and infection by AAV vector.

DNA damaging agents of the present invention include those which cause dimerization of adjacent nucleotides, scission of at least one DNA strand, as well as alkylating agents. Such agents include radioactive molecules, including tritiated nucleotides such as thymidine (scission), ultraviolet (UV) irradiation (dimerization), gamma irradiation (scission) and cis-platinum (alkylation). It will also be appreciated that DNA damaging agents at appropriate levels will also generally induce DNA repair. Agents which damage chromosomal integrity include not only those which physically damage the DNA strands, but those which disrupt chromosomal integrity, such as topoisomerase inhibitors. Preferred agents of this class are etoposide and camptothecin, which have been used clinically as oncotherapeutics. Additionally, agents affecting DNA synthesis, which include ribonucleotide reductase inhibitors such as hydroxyurea, and DNA polymerase inhibitors such as aphidicolin, are suitable for use in the method of the present invention. It will also be appreciated that different agents may have more than one effect on DNA metabolism, and that more than one agent can be employed sequentially or concurrently. It will also be appreciated that both animal and human cell populations can be treated in accordance with the methods of the present invention to increase transduction by AAV vectors.

The methods of the present invention increase transduction by recombinant AAV vectors and thus expression of the transferred genetic material. Thus, the methods described herein can be utilized to increase levels of production of a desired heterologous gene product or protein in cell culture. Increased transduction is particularly useful in populations of terminally differentiated or non-dividing cells such as hematopoietic stem cells, neurons, quiescent lymphocytes and normal epithelial cells, to facilitate production of cell-specific product. It will be appreciated by those skilled in the art that any polynucleotide or gene of interest suitable for transfer via a recombinant AAV vector can be employed. Methods for recombining genetic material are well known to those skilled in the art and can be accomplished by utilizing conventional recombination technology. See Sambrook J. et al., *Molecular Cloning,* Cold Spring Harbor Laboratory Press, Cold Spring Harbor, N.Y. (1989). The preparation of AAV vectors carrying human therapeutic genes, such as, for example, globin genes and the cystic fibrosis transmembrane conductance regulator (CFTR) gene, can also be accomplished using approaches and recombination schemes known to or easily devised by those skilled in the art. See Walsh et al., *Proc. Natl. Acad Sci. U.S.A.* 89, 7257–7261 (1992); and Flotte et al., *Proc. Natl. Acad Sci U.S.A.*, 90, 10613–10617 (1993).

In addition to the increased manufacture of a desired gene product, increased transduction in accord with the methods of the present invention provides for improved therapeutic applications of the vector. For example, in the ex vivo treatment of cell populations removed from a patient, wherein the cells are treated with recombinant vector carrying the therapeutic gene, then reimplanted into the patient, treatment of the cell population ex vivo with transduction-increasing agents of the present invention can improve the efficacy of such treatments. With respect to in vivo or direct therapy, the patient or target site or tissue can be treated with agents of the invention to enhance transduction by the AAV recombinant vector carrying the therapeutic gene. Again this approach is particularly useful when the target cell population comprises terminally differentiated or non-dividing cells such as, for example, neuronal, hepatic and airway epithelial cells.

Further applications of the method of the present invention include screening the activity of therapeutic genes in terminally differentiated or non-dividing cell populations by treating such cell populations ex vivo to enhance transduction, thereby allowing the testing of gene function in the cell population. Similarly, cell cycle check point genes, i.e. genes affecting cell division or the cell cycle, such as mammalian homologs of the yeast cdc genes, can be screened for therapeutic potential. The method of the present invention is also currently being utilized to screen other vectors, such as retroviral vectors, for their ability to transduce non-dividing cells, using AAV transduction in accord with the invention as a positive control for transduction. The method of the present invention further provides an assay for agents that influence or alter nucleic acid metabolism, including DNA damage, DNA repair, DNA synthesis and chromosomal integrity, by testing whether they increase transduction over untreated negative controls and positive controls of AAV transduction of the invention. Conversely, transduction-increasing agents can also now be preselected on the basis of their impact on nucleic acid metabolism, and then assayed for levels of increase in transduction over untreated negative controls and positive controls of transduction of the invention.

Preferred agents of the method of the present invention are those with the greatest effect on transduction and the least toxicity. It will be appreciated that this may vary depending on the application, for example whether ex vivo or in vivo. It will also be appreciated that different cell types may respond differently to different agents. One skilled in the art can thus select the appropriate agent (and dosage as described below) depending upon the intended use, weighing efficacy, toxicity, and the nature of the target cell population as three major factors in the selection process. For example, etoposide and camptothecin have been delivered in vivo as oncotherapeutics at the required doses with acceptable toxicities. Hydroxyurea treatment ex vivo also has no measurable toxicity at the doses used. Agents that cause less DNA damage, such as hydroxyurea and etoposide, respectively, would thus be currently preferred, with etoposide preferred for in vivo use.

Dosage ranges of selected agents of the present invention which have been utilized are preferably as follows: tritiated thymidine—from about 1 $\mu$Ci/ml to at least 10 $\mu$Ci/ml; UV irradiation—from about 25 to at least about 50 joules/msq; gamma irradiation—from about 250 to about at least 4000 rad, and preferably about 2000–4000 rad; etoposide—from greater than 0 to about 100 $\mu$M, preferably about 1–30 $\mu$M, and more preferably 3 $\mu$M or less; camptothecin—from greater than 0 to about 30 $\mu$M, and preferably about 0.1–10 $\mu$M; hydroxyurea—from about 0.40 mM to at least about 40.00 mM; and aphidicolin at about 5 $\mu$g/ml. The doses administered can, of course, vary, generally determined by the level of enhancement of transduction and expression balanced against any risk or deleterious side effect, by whether the use is ex vivo or in vivo, and the factors described above. Monitoring levels of transduction and expression can also assist in selecting and adjusting the doses administered.

COMMERCIAL UTILITY

Cells or cell populations, particularly of non-dividing or terminally differentiated cells, can be treated in accordance with the present invention ex vivo or in vivo to increase their transduction by AAV recombinant vectors. As described herein, by increasing transduction of cell populations, the manufacture of specific desired proteins can be increased. Desirable products include clotting factors, globin gene products, cytokines and growth factors. Treatment to increase transduction in accord with the present invention also has therapeutic applications, improving transduction and therefore efficacy of in vivo and ex vivo treatment of patient cell populations and target tissues with recombinant AAV vectors. Other vectors can be screened for transduction effectiveness using transduction of the invention as a positive control. The methods of the invention additionally provide an assay for DNA metabolism-altering agents by measuring increases in levels of transduction by these agents. Transduction-increasing agents can also now be preselected by their effect on various aspects of DNA metabolism, then assayed for levels of transduction by employing the methods of the present invention. Ex vivo screening for function of a gene, particularly in non-dividing cells such as stationary fibroblasts or neuronal cells, can also be more easily accomplished in the appropriate cell type with increased transduction according to the methods of the invention.

EXAMPLES

The Examples presented below are provided as a further guide to the practitioner of ordinary skill in the art, and are not to be construed as limiting the invention in any way.

MATERIALS AND METHODS

The Examples provided below utilized the following methods, unless otherwise specified.

Cell culture. Hela cells and 293 cells have been described by Gey G. O. et al., *Cancer Res.* 12, 264 (1952) and Graham F. L. et al., *J Gen. Virol.* 36, 59–72 (1977). Neonatal primary human foreskin fibroblasts were kindly provided by Dr. Christine Halbert and Dr. Theo Palmer having been isolated as described by Limon J. et al., *Cancer Genet. Cytogenet.* 23, 305–313 (1986) or Palmer, T. D. et al., *Proc. Natl Acad Sci. U.S.A.* 84, 1055–1059 (1987). Cells were maintained in Dulbecco's modified Eagle medium (DMEM) supplemented with 10% heat inactivated (30 min at 56 degrees C) fetal bovine serum (FBS), 100 units/ml penicillin, 100 $\mu$g/ml streptomycin and 2.5 $\mu$g/ml amphotericin B. Cultures were grown in 10 cm dishes (Corning) at 37 degrees C. in 10% $CO_2$. Stock Hela and 293 cells were passaged weekly by treatment with trypsin (0.05%) EDTA (0.53 mM) and replated at cell densities appropriate for continuous exponential growth. Stock primary human fibroblast cultures were established from frozen stocks at passage 4 and maintained in culture by weekly passage for up to 10 additional passages. Each passage entailed a 1 in 2 split with one culture being maintained as stock and the other used for experimentation. Stationary cultures of primary human fibroblasts were prepared in 6 cm dishes (Corning) or in 6 well plates Falcon) as described below.

Stationary cultures were prepared by changing the medium in confluent cultures to DMEM containing 5% heat-inactivated FBS and $10^{-6}$M dexamethasone, and maintaining these cultures for at least two weeks while replacing the medium every 3–4 days. Dividing cultures were prepared by treatment with trypsin and plating the cells at a density of either $2.5 \times 10^5$ cells per 35 mm well in 6 well plates (Falcon) or at $4 \times 10^5$ cells per 60 mm dish (Corning) the day before infection.

Vector construction, production and assay. The plasmid pALAPSN used to generate the AAV vector AAV-LAPSN has been described Russell, D. W. et al., Proc. Natl. Acad. Sci. U.S.A 91:8915–8919, 1994)). The plasmids pTR, pTRneo, and pTRAAVneo were kindly provided by Dr. Sergei Zolotukhin and Dr. Nicholas Muzyczka, and were derived from the vector plasmid d13–94 described by McLaughlin, S. K. et al., *J Virol* 62, 1963–1973 (1988). Plasmids pTR and pTRNEO are vector cloning constructs containing no insert or the SV40 early promoter and neomycin resistance gene (neo), respectively. pTRAAVNEO is a helper construct containing the AAV terminal repeats (Samulski R. J. et al., *Proc. Natl. Acad. Sci U.S.A.* 79, 2077–2081 (1982)), the MLV LTR promoter (Weiss R. et al., *RNA tumor viruses.* Cold Spring Harbor Laboratory Press, Cold Spring Harbor, N.Y., p. 766 (1985)), the human placental alkaline phosphatase gene (Kam W. et al., *Proc. Natl. Acad. Sci. USA.* 82, 8715–8719 (1985)), the SV40 early promoter (Reddy V. B. et al., *Science* 200, 494–502 (1978)), the neo gene (Beck E. et al., *Gene* 19, 327–336 (1982)) and the SV40 polyadenylation signal (sequence available on request). Plasmids pPTRNEO and pALAPSN propagated in the bacterial stain JC8111 (Boissy R. et al., *Gene* 35, 179–185 (1985)) were used to generate vector stocks of AAV-SVNEO and AAV-LAPSN respectively as described previously by Hermonat, P. L. et al., *Proc. Natl. Acad. Sci. USA.,* 81, 6466–6470 (1984). When necessary, vector stocks were concentrated as described by Ruffing M. et al., *J Virol.* 66, 6922–6930 (1992). Based on the infectious center assay of Yakobson, B. et al., *J Virol.* 61, 972–981 (1987), this method produced stocks with wild type virus titers at approximately 2% of vector titers. AAV vector particle numbers were determined by quantification of purified vector DNA on Southern blots probed with vectors sequences. The retroviral vector LAPSN (Miller, D. G. et al., *Proc. Natl. Acad Sci. U.S.A.* 91, 78–82 (1994)) is analogous to the AAV vector AAV-LAPSN and was generated in PA317 packaging cells (PA317/LAPSN) as described by Miller, A. D. et al. (*Biotechniques* 7, 980–990 (1989)).

The plasmid pALβgeo used to generate the AAV vector AAV-Lβgeo was constructed using standard molecular techniques from the plasmid pTR discussed above. Plasmid pALβgeo contains the following sequences inserted in the Pst 1 site of pBR322 in the following order: the AAV2 ITR in the flip orientation (Samulski R. J. et al., *Proc. Natl. Acad Sci. USA.* 79, 2077–2081 (1982)), an Nhe I—Kpn I fragment of Moloney murine leukemia virus containing the retroviral promoter (Weiss R. et al., (eds) *RNA Tumour Viruses.* 766, Cold Spring Harbor Laboratory Press, Cold Spring Harbor, N.Y., (1985)), the fusion gene βgeo encoding both β-galactosidase and neomycin phosphotransferase (Friedrich G. et al., *Genes and Develop.* 5, 1513–1523 (1991), nucleotides 2613 to 2570 of SV40 containing the polyadenylation signal (Genbank accession #V10380), and the AAV2 ITR (flip orientation). The final size of the recombinant vector genome was 4781 bases i.e., 102% wild-type size. Plasmids were propagated in the bacterial strain JC8111 (Boissy R. et al., *Gene* 35, 179–185 (1985)) and vector stocks were generated as previously described above.

Analysis of alkaline phosphatase expression. Enzyme histochemistry was performed as described by Fields-Berry S. C. et al., *Proc. Natl. Acad Sci. USA.* 89, 693–697 (1992). Cell lysates for alkaline phosphatase assay were prepared essentially as described by Berger J. et al., *Proc. Natl. Acad Sci. USA.* 84, 4885–4889 (1987). Cell monolayers were washed twice with Dulbecco's phosphate buffered saline (PBS), scraped into 3 mls of homogenization buffer (10 Mm Tris. Hcl Ph 7.4, 1.0 Mm $MgCl_2$, 20 $\mu$M $ZnSO_4$) using a rubber policeman and pelleted at 1000 xg for 5 min. The cell pellet was resuspended in 500 $\mu$l of homogenization buffer, sonicated briefly, mixed with 214 $\mu$l of 1-butanol and allowed to stand at room temperature for 2 hours. After brief centrifugation the lower aqueous phase was removed and incubated at 65 degrees C. for 10 minutes. Lysates were stored at –20 degrees C. until assayed. Alkaline phosphatase activity in cell lysates was determined using a spectrophotometric assay as described by Berger J. et al., *Gene* 66, 1–10 (1988). Ten to 100 $\mu$l of lysate was brought to a final volume of 100 $\mu$l with homogenization buffer and diluted with 100 $\mu$l of 2X SEAP buffer (2.0 M diethanolamine Ph 8.0, 1.0 mM $MgCl_2$). Twenty $\mu$l of p-nitrophenyl phosphate (120 MM in 1X SEAP buffer) was added to initiate the assay. The OD at 405 nm was then followed as a function of time. Controls included a blank with no cell lysate and cell lysates from uninfected cultures. The protein content of each sample was determined using the method of Bradford M. M. *Anal. Biochem.* 72, 248–254 (1976).

Analysis of β-galactosidase expression. β-galactosidase expression was measured by cellular staining. Cells were washed once with PBS, fixed in 3.4% formaldehyde in PBS, and was washed three times with PBS over thirty minutes. The cells were then stained in 5 mM $K_3Fe(CN)_6$, 5 mM $K_4Fe(CN)_6 3H_2O$, 2 mM $MgCl_2$, and 1 mg/ml 5-bromo-4-chloro-3-indolyl β-D-galactopyranoside in PBS for eight hours at 30° C.

Physical and chemical treatments. Cells were exposed to gamma irradiation at 364 rad/minute from a $^{137}$Cs source by using a Model M38-1 gammator (Radiation Machinery Corporation) and UV (254 nm) irradiated using a Stratalinker UV cross-linker (Stratagene) immediately before addition of vector. Thymidine [methyl-$^3$H] (Dupont-NEN 82–89 Ci/mmol) was incubated with experimental cultures from the time of vector addition until analysis of alkaline phosphatase expression 48 hours later. Cultures were preincubated with cis-platinum(II)-diamine dichloride, hydroxyurea, etoposide, camptothecin, aphidicolin, actinomycin D, novobiocin, or cyclohexamide (all from Sigma) for 16 hours and then washed twice with fresh medium prior to addition of vector. Cultures were treated with nocodazole (Sigma) from 1000-fold concentrated stocks dissolved in dimethylsulfoxide. Cultures were incubated with nocodazole from 2 hours prior to vector addition until analysis of alkaline phosphatase expression 48 hours later. Cultures were treated with methotrexate (Sigma) from 100-fold concentrated stocks dissolved in 50 mM$NaHCO_3$ in standard DMEM without dialyzed FBS. Cultures were preincubated with methotrexate for 20 hours, then washed twice with fresh medium prior to vector addition.

Autoradiography. Tritium labeling and analysis of S-phase cells was performed as follows: Cultures were labeled with 10 $\mu$Ci/ml $^3$H-thymidine (Dupont-NEN, 89 Ci/mmol) using dialyzed, heat-inactivated FBS. After labeling, cells were either stained or washed and cultured in the presence of 20 $\mu$M non-radioactive thymidine until staining. Cultures were first stained for alkaline phosphatase (Fields-Berry, S. C. Halliday, A. L. & Cepko, C. L. Proc. Natl. Acad Sci. U.S.A. 89, 693–697 (1992)), rinsed with distilled water, treated with cold 5% trichloroacetic acid and processed for autoradiography as described by Miller, D. G. et al., Mol. Cell. Biol. 10, 4239–4242 (1990), then counterstained with nuclear fast red (1 mg/ml in 5% aluminum sulfate) to identify unlabeled nuclei.

DNA manipulations and analysis. AAV vector DNA was purified by the procedure of Samulski, R. J. et al., J Virol. 63, 3822–3228 (1989). Isolation of episomal AAV vector DNA from stationary cultures was performed using a modification of the procedure described by Hirt B., J Mol. Biol. 26, 365–369 (1967). Episomal and high molecular weight DNAs were fractionated as described by Hirt, followed by Proteinase K digestion, extraction with phenol, chloroform and butanol, and ethanol precipitation. All cultures used for DNA isolation were washed the day of the infection, and immediately prior to DNA purification, to remove extracellular vector particles. Southern blot analysis was performed using standard procedures described by Sambrook J. et al., Molecular Cloning. Cold Spring Harbor Laboratory Press, Cold Spring Harbor, N.Y. (1989).

EXAMPLE 1

Effect of DNA Damaging Agents on Transduction Efficiency of AAV-LAPSN and AAV-L$\beta$geo The following Example shows that DNA damaging agents increase the transduction efficiency of the vectors AAV-LAPSN and AAV-L$\beta$geo. The vector AAV-LAPSN contains the human placental alkaline phosphatase gene driven by the Moloney murine leukemia virus LTR promoter and the neo gene driven by the SV40 early promoter. Four agents were tested, ultraviolet light (254 nm), gamma irradiation, tritiated thymidine, and the alkylating agent cis-platinum.

For UV irradiation, cultures were exposed to 0 joules/msq, 10 joules/msq, 25 joules/msq, or 50 joules/msq of UV irradiation immediately prior to the addition of vector. Cultures were exposed to gamma irradiation at 0 rad, 250 rad, 500 rad, 1000 rad, 2000 rad, or 4000 rad immediately prior to vector addition. For treatment with tritiated thymidine, cultures were exposed to 0 $\mu$Ci/ml, 0.1 $\mu$Ci/ml, 1 $\mu$Ci/ml or 10 $\mu$Ci/ml of tritiated thymidine from the time of vector addition to the end of the 48 hour incubation period. Cultures were pre-incubated with 0 nM, 10 nM, 100 nM, 1000 nM, or 10000 nM of cis-platinum (II)-diamine for 16 hours prior to vector addition.

The effect of each agent on transduction was determined by examining the relative number of alkaline phosphatase-positive staining cells in treated and untreated stationary primary human fibroblast cultures 48 hours after infection with the vector AAV-LAPSN. Generally, stocks of the vector AAV-LAPSN contained about 100 or 2000 AP focus-forming units per ml when assayed on stationary or dividing fibroblast cultures, respectively. Vector particle numbers usually were determined by quantifying the full-length single-stranded vector genome signal on Southern blots of purified vector DNA preparations. Vector stocks were prepared by published techniques (Russell et al., Proc. Natl. Acad Sci. U.S.A. 91, 8915 (1994); Hermonat et al., Proc. Natl. Acad Sci. U.S.A. 81, 6466 (1984), which are hereby incorporated by reference).

Each of the four agents tested markedly increased the transduction efficiency of AAV-LAPSN. Treatment with tritiated thymidine showed a significant increase in relative transduction efficiency beginning at the 1 $\mu$Ci/ml dose. For cis-platinum pretreatment, the relative transduction efficiency increased beginning at a dose of 100 nM. The relative transduction efficiency increased at a dose of 25 joules/msq for UV-irradiated cells, and 250 rad for gamma irradiated cells. At the maximum doses tested the increase ranged from 20- to 90-fold. Similar results were obtained when two independent experiments were performed.

In a separate study, gamma irradiation also increased the transduction efficiency of a second vector, AAV-L$\beta$geo. AAV-LAPSN contains the Moloney murine leukaemia virus promoter (MLV) (Weiss R. et al., ibid.), the human placental alkaline phosphatase gene (AP) (Kam W. et al., ibid.), the SV40 early promoter (SV) (Reddy V. B. et al., ibid.), and the neomycin phosphotransferase gene (neo) (Beck E. et al., ibid.). AAV-L$\beta$geo contains the MLV promoter, the fusion gene $\beta$geo, and the polyadenylation signal flanked by the inverted terminal repeat (ITR) sequences. The cultures were exposed to gamma irradiation at the doses and as described above. Data generated using the vector AAV-L$\beta$geo demonstrated that the transduction efficiency of a second AAV vector using a different reporter gene is also increased by gamma irradiation. Increased efficiency was seen with doses as low as 250 rad, with over a hundred-fold increase observed with a dose of 4000 rad.

EXAMPLE 2

Effect of Nocodazole and Methotrexate on Transduction Efficiency of AAV-LAPSN

Two cytotoxic agents that do not directly damage DNA were tested using cells and vectors described in Example 1. The cytotoxic agents were nocodazole, an inhibitor of mitotic spindle formation and methotrexate, a folic acid antagonist. At nocodazole concentrations ranging from 50 ng/ml to 1 $\mu$g/ml, all of which produced mitotic arrest, there was little or no effect on transduction efficiency. Similarly methotrexate had no effect on transduction efficiency over the concentration range $10^{-4}$ to $10^{-9}$ molar. The failure of nocodazole to block transduction is also consistent with our earlier conclusion that mitosis is not required for transduction by AAV vectors.

EXAMPLE 3

Effects of Actinomycin D and Cyclohexamide on Transduction Efficiency of AAV-LAPSN.

Primary human fibroblasts were treated with metabolic inhibitors that target transcription and translation to determine whether these would effect the efficiency of transduction by adeno-associated virus vectors. Stationary fibroblast cultures were chemically treated for 16–20 hour overnight incubations. The chemicals were removed from the cells by two washes with DMEM. After the second wash, AAV-LAPSN was added for transductions. Transduction level was measured by histochemical staining two days after transduction. No increase in transduction was observed after treating stationary human fibroblasts overnight with 2 or 10 $\mu$g/ml of actinomycin D, a drug that inhibits transcription, nor after inhibiting protein synthesis with 10 μg/ml of cyclohexamide. These results indicated that when increased transduction was seen with other drugs tested, the increase did not reflect an indiscriminate cellular response that resulted from any type of metabolic insult. A somewhat decreased transduction was observed after actinomycin D treatment that may have resulted from cytotoxic effects of the drug, particularly as treatment with either dose of actinomycin D also prevented transduction by retroviral vectors.

EXAMPLE 4

Stability of the Transduced Reporter Gene

The absolute number of alkaline phosphatase-positive cells in gamma irradiated (4000 rad) stationary primary human fibroblast cultures was followed for 14 days after infection with AAV-LAPSN. Alkaline-phosphatase-positive (AP-positive) cells were tallied at 2, 5, 7, and 14 days post-infection. The increase in AP-positive cells was approximately linear during the 14 days. During the 14-day period the absolute number of alkaline phosphatase-positive cells increased 11-fold between 2 and 14 days post-infection. The fold increase in transductants in irradiated cultures above control levels in unirradiated cultures was 53- and 78-fold at 2 and 9 days post-infection, respectively.

EXAMPLE 5

Increased Transduction of Dividing and Non-Dividing Cells by Tritiated Thymidine In the two independent cultures treated with 10 microcuries/ml (μCi/ml) of tritiated thymidine (Example 1) it was possible to determine which of the alkaline phosphatase-positive cells had been transduced independent of both S phase and mitosis by coating the stained monolayers with nuclear emulsion and performing autoradiography as described above in the Materials and Methods. Double labeled cells represent the population that were in S phase at some point during the period in which transduction occurred (S phase transductants). Cells labeled with alkaline phosphatase alone represent the population of cells that were transduced independent of S phase (non-S phase transductants).

Using this technique it was determined that in these two cultures 10% of transduction events occurred independent of both S phase and mitosis. Since the presence of 10 μCi/ml of tritiated thymidine in these cultures caused a mean increase in transduction efficiency of 18-fold, the absolute number of transduction events occurring independent of both S phase and mitosis exceeded the total number of transduction events occurring in control cultures that did not receive tritiated thymidine (10% of 18 is greater than 1). This result demonstrated that the presence of tritiated thymidine in the cultures increased the transduction efficiency of non-dividing cells. However, because tritiated thymidine increases the transduction of non-S phase cells, the magnitude of the increase in non-dividing cell transduction cannot be calculated using autoradiography.

EXAMPLE 6

Effect of DNA Damaging Agent Gamma Irradiation on the Transduction of Dividing and Non-Dividing Cells To further define the effect of DNA damaging agents on the transduction of non-dividing cells, gamma irradiation was combined with a second agent. Cultures of stationary primary human fibroblasts were gamma irradiated with doses ranging from 250 to 4000 rad 8 hours prior to addition of 10 μCi/ml tritiated thymidine and AAV-LAPSN vector, followed by alkaline phosphatase staining and autoradiography 48 hours later. Controls included no treatment, vector alone, tritiated thymidine alone and vector with tritiated thymidine. The 8-hour interval between irradiation and exposure to vector and tritiated thymidine was employed to reduce the proportion of dividing cells in the culture. In the control culture that did not receive gamma irradiation, tritiated thymidine labeling revealed that 6% of cells were in S phase at some point during the period of vector exposure, while less than 2% of cells in the culture receiving 4000 rad were in S phase at some point during the same period. Lower doses of irradiation gave intermediate values.

An increase in both S and non-S phase transductants was observed with increasing doses of gamma irradiation. The increase in transduction efficiency of non-S phase cells ranged from 7-fold at 250 rad to an excess of 100-fold at 4000 rad. The effect of irradiation on the transduction efficiency of S phase cells was much less marked and was only apparent at radiation doses of 2000 rad and above. If these data are recalculated, using values obtained from a control culture receiving no tritiated thymidine, increases in transduction efficiencies up to 750-fold are obtained for non-S phase cells. These higher fold increases in transduction efficiency represent the combined effect of tritiated thymidine and gamma irradiation and are based on the assumption that 10% of the transduction events in the control culture occurred independent of S phase. This value is based on previous work and is likely to be an overestimate.

EXAMPLE 7

Comparison of Expression of Alkaline Phosphatase from Gamma Irradiated and Non-Irradiated Fibroblasts In order to eliminate the possibility that the results described in the Examples above resulted from increased expression rather than increased transduction, the following study was performed. Polyclonal cultures of G418-selected primary human fibroblasts transduced with AAV-LAPSN were exposed to 4000 rad of gamma irradiation and 48 hours later the alkaline phosphatase expression was compared to unirradiated cultures. One culture from each treatment group was fixed and stained for alkaline phosphatase, and the alkaline phosphatase activities in cell lysates were determined for 2 cultures. There was no difference in the number of cells expressing alkaline phosphatase in irradiated and unirradiated cultures.

The effect of gamma irradiation on alkaline phosphatase expression from the G418 selected polyclonal population of primary human fibroblasts transduced with AAV-LAPSN was examined. Replicate cultures in each treatment group were: control naive primary human fibroblasts, transduced unirradiated fibroblasts, and transduced fibroblasts 48 hours after 4000 rad of gamma irradiation.

Quantitative analysis of alkaline phosphatase activity revealed that irradiation caused a modest fall in alkaline phosphatase expression. These data are consistent with the conclusion that the increased transduction efficiency of AAV-LAPSN following irradiation is not due to increased expression from transductants expressing alkaline phosphatase activity at levels not detectable by the histological staining method used.

EXAMPLE 8

Assessment of Episomal Vector DNA Amplification

The following study demonstrated that episomal vector DNA amplification does not explain increased transduction. Helper virus-independent amplification of wild-type adeno-associated virus DNA has been reported to occur following genotoxic stress (Yalkdinoglu A. O. et al., Cancer Res. 48, 3124–3129 (1988)). More than 400-fold amplification has been observed in CHO-K1 cells following treatment with the mutagen N-methyl-N'-nitro-N-nitrosoguanidine (MNNG) and a 30-fold amplification in human diploid fibroblasts (E6). To determine whether a similar phenomena might accompany the increased transduction efficiency of AAV vectors in cells exposed to DNA damaging agents, Hirt supernatants from both irradiated and unirradiated cultures of stationary primary human fibroblasts were assayed 48 hours following vector exposure. Quadruplicate cultures received either no treatment, vector alone or both 4000 rad of gamma irradiation and vector. At 48 hours low molecular weight DNA was isolated from triplicate cultures in each treatment group. The fourth culture in each group was stained for alkaline phosphatase-positive cells to determine the increase in transduction efficiency caused by the gamma irradiation, which was in excess of 100-fold. An autoradiograph of low molecular weight DNA isolated from triplicate stationary cultures of primary human fibroblasts in each of three treatment groups was made. The groups were control uninfected cultures, unirradiated cultures infected with AAV-LAPSN and cultures infected with AAV-LAPSN after 4000 rad of gamma irradiation. Briefly, Hirt supernatant DNA, which was harvested from the triplicate cultures from each treatment group 48 hours after infection, was subjected to Southern analysis using a neo probe. A phosphoimager was used to quantitate the total hybridization signal in each lane, and the signal representing the single stranded monomer forms of vector DNA. The maximum variation between lanes was 45% i.e., within experimental error. The results revealed no evidence of significant DNA amplification in gamma irradiated cultures. These data demonstrated that the increased transduction efficiency of AAV vectors in irradiated cells was not due to marked amplification of episomal vector DNA.

EXAMPLE 9

Measurement of Cytotoxicity of Gamma Irradiation

The ability of primary human fibroblasts to form colonies following gamma irradiation was examined to determine if increased transduction occurs at radiation. doses that could be applied clinically, particularly in vivo. Stationary monolayer cultures of primary human fibroblasts were exposed to gamma radiation over the dose range 250 to 4000 rad. Twenty-four hours after irradiation cultures were treated with trypsin and replated at low density. After a further 8 days colonies were fixed, stained with Coomassie blue and counted. All doses tested caused a reduction in colony formation. The gamma irradiation dose that reduced colony formation to approximately 50% of control levels was 450 rad. Nine days post-irradiation there was no appreciable difference in the viability of cells receiving 4000 rad and unirradiated cells as determined by trypan blue exclusion.

EXAMPLE 10

Effect of Hydroxyurea on Transduction of Cells by AAV-LAPSN

Dividing and stationary primary human fibroblast cultures were prepared as described above. Cultures were pretreated with hydroxyurea at 0, 0.4, 4, and 40 mM for 16 hours, washed twice with fresh medium, then exposed to AAV-LAPSN vector stocks. Staining for alkaline phosphates was performed 48 hours later. Experiments were performed in triplicate, and relative titers were determined by comparing the number of cell foci expressing alkaline phosphatase in treated cultures with the number observed in control untreated cultures. The relative titer was observed to increase with increasing doses of hydroxyurea. For stationary cultures, treated with doses at 0.4, 4, and 40 mM the increases in relative titer were about 3–4, 60, and 300, respectively. For stationary cultures treated with the same doses of hydroxyurea, the relative titers increased by about 3, 20, and 40, respectively. When titers/ml were compared for stationary and non-stationary treated cultures, it was apparent that hydroxyurea treatment tended to obviate the differences in titer obtained with the two types of cells when untreated. The comparison showed that the transduction enhancing effect was greater for stationary than for dividing cells. For the optimal dose of 40 mM hydroxyurea enhanced transduction in stationary cells by a factor of about 200, while the drug enhanced transduction in dividing cells by only a factor of about 35. In the absence of treatment, over ten-fold higher titers were obtained using dividing cultures, but with 40 mM hydroxyurea, only about a three-fold difference was obtained.

EXAMPLE 11

Effect of Hydroxyurea on Stationary Human Fibroblast Viability

Stationary human fibroblast cultures were exposed to hydroxyurea at the concentrations indicated in the previous Example, then treated with trypsin, plated at different dilutions in fresh media, allowed to proliferate until colonies were clearly visible, then the number of viable colony forming units per well (CFU/well; 6 well plate) were determined. The experiment was performed in triplicate using different concentrations of hydroxyurea as indicated in Table 1 below. Shown are the CFU/well, average CFU/well for each treatment (AVG), standard deviation (SDEV) and standard error (SE).

TABLE I

HYDROXYUREA KILL CURVE
Effect of hydroxyurea (HU) on stationary
human fibroblast cell viability

| mM HU | CFU/well | AVG | SDEV | SE |
|---|---|---|---|---|
| 0.00 | 768,000 | | | |
| 0.00 | 480,000 | | | |
| 0.00 | 592,000 | | | |
| | | 613,333 | 145,180 | 83,919 |
| 0.40 | 544,000 | | | |
| 0.40 | 576,000 | | | |
| 0.40 | 576,000 | | | |
| | | 565,333 | 18,475 | 10,679 |
| 4.00 | 448,000 | | | |
| 4.00 | 752,000 | | | |
| 4.00 | 560,000 | | | |
| | | 586,667 | 153,744 | 88,870 |
| 40.00 | 608,000 | | | |
| 40.00 | 624,000 | | | |
| 40.00 | 608,000 | | | |
| | | 613,333 | 9,238 | 5,340 |

The results shown in Table 1 above indicate that the viability of the cells was essentially unaffected by hydroxyurea within a range of about 0.40 to 40.00 mM.

EXAMPLE 12

Effect of Etoposide on Transduction by AAV

Stationary human fibroblast cultures were prepared and AAV-LAPSN stocks were titered as in Example 10, except that etoposide at 0, 3, 10, 30, or 100 μM was used instead of hydroxyurea. Two independent experiments were performed, and titers relative to untreated cultures were determined after transducing treated and untreated stationary cells. An increase in the relative titer was observed for all doses tested. The greatest relative increase observed was 40- to 50-fold, and was obtained using 3 μM etoposide. Lower doses were somewhat less effective, with increases in relative titer of 30- to 45-fold for 10 μM, and around 20-fold for doses of 30 μM or 100 μM.

In other experiments, the effects of etoposide on stationary and dividing cells were compared. Cultures, both stationary and dividing, were treated overnight with 0, 0.3, 1, 3, 10, and 30 μM etoposide followed by transduction with AAV-LAPSN. Measurable increases in transduction (measured as described above) by AAV-LAPSN were observed for all doses tested in both types of culture, but the effects were most pronounced in doses above 3 μM. Results were generally similar to those obtained using hydroxyurea, as described in Example 11. At etoposide doses above 3 μM, the transduction efficiencies of stationary cultures were only 3–4 fold lower than dividing cultures, and titers were higher than untreated dividing cultures. There was no decrease in the viability of stationary fibroblasts treated with this dose as measured by a colony-forming assay. Similar transduction increases also occur in normal human respiratory epithelial cells treated with etoposide.

EXAMPLE 13

Effect of Aphidicolin on Transduction by AAV

Stationary human fibroblast cultures were prepared and AAV-LAPSN stocks were titered as in Example 10, except that aphidicolin was used instead of hydroxyurea. Aphidicolin, a DNA polymerase inhibitor, at 5 μg/ml increased AAA-LAPSN titers 18.6 fold relative to untreated cultures. Hydroxyurea, which prevents DNA synthesis by inhibiting ribonucleotide reductase and depleting deoxynucleotide pools (Thelander and Reichard, *Annu. Rev. Biochem.* 48, 133–158 (1979)) was shown to increase transduction efficiency of AAV-LAPSN over 300-fold. In a similar manner, a transduction increase was observed after an overnight pretreatment with 1 mM 2'-deoxyadenosine. This result was consistent with the ability of 2'-deoxyadenosine to inhibit ribonucleotide reductase. However, abnormally high nucleoside levels could influence many biochemical pathways. Taken together, these results suggested that prior exposure of stationary cultures to drugs that inhibit DNA synthesis increases transduction by AAV vectors.

EXAMPLE 14

The Effects of Topoisomerase Inhibitors on Transduction by AAV Vectors

The topoisomerase inhibitor etoposide was shown to increase transduction by AAV vectors. Topoisomerase inhibitors affect many aspects of DNA metabolism, including replication, recombination and repair. The transduction effect of etoposide was compared with the intercalator amsacrine, which like etoposide inhibits type II topoisomerase and enhances enzyme-mediated DNA cleavage (Liu, *Ann. Rev. Biochem.* 58, 351–375, 1989); novobiocin, which inhibits type II topoisomerase by interacting with the ATP binding site (Osheroff et al., *J Biol. Chem.* 258, 9536–9543, 1983) and camptothecin, which is a type I topoisomerase inhibitor that produces DNA strand breaks (Liu, ibid.). Stationary fibroblast cultures were exposed to each of the four topoisomerase inhibitors at .01 μM, 0.1 μM, 0.3 μM (for etoposide only), 1 μM, 3 μM, 10 μM and 30 μM overnight. The inhibitors were washed from the cells, and the cells were transduced with AAV-LAPSN. The relative transduction efficiency was determined by histochemical staining. Pretreatment of stationary fibroblast cultures with 3 μM etoposide or 0.1 μM camptothecin increased the transduction efficiency of AAV-LAPSN more than 50 fold. Amsacrine and novobiocin had no significant effect on transduction over the range of concentrations, and doses over 30 μM produced cell death in stationary cultures. It is not clear why enhanced transduction occurs with some topoisomerase inhibitors and not with others, especially given that etoposide and amsacrine are structurally similar. However, these two drugs do have mechanistic differences, and they produce strand breaks at different chromosomal sites, so there may be specific drug interactions that mediate or prevent increased transduction.

EXAMPLE 15

Hydroxyurea and Etoposide Increase the Number of Stable Transductants Produced by AAV Vectors.

It is not known if transduction by AAV vectors requires integration, and it is possible that AP expression occurs transiently from episomal vector genomes. A better measure of vector integration is transduction of G418 resistance because it requires stable gene expression, and G418-resistant fibroblasts transduced by AAV-LAPSN contain integrated vector sequences.

Stationary fibroblast cultures were exposed overnight to either 40 mM hydroxyurea or 2.0 μM etoposide. A control culture was left untreated. After the overnight exposure the cells were washed and infected with AAV-LAPSN (day 1). On day 2, the cultures were treated with trypsin, and the cells were plated at different dilutions in DMEM with 10% FBS. G418 was added to the cultures on day 3 as described by Russell et al. (*Proc. Natl. Acad Sci. USA* 91: 8915–8919, (1994)). The relative transduction efficiency was determined by dividing the number of transductants/ml of vector stock produced after each drug treatment by the number of transductants/ml of vector stock in untreated cultures. Efficiency of transduction using alkaline phosphatase staining was carried out as described previously.

The results demonstrated that hydroxyurea and etoposide not only affected AP expression, but also increased the transduction of G418 resistance in stationary fibroblast cultures, suggesting that these agents stimulate the integration of AAV vectors. The effects were smaller than those observed for AP expression, probably because the G418 resistance assay requires that stationary cultures be stimulated to divide during the selection period, resulting in higher transduction efficiencies in untreated cultures.

The persistence of reporter gene expression was also measured by following the time course of AP expression after infection with AAV-LAPSN. Transduction efficiencies were shown to increase over time in stationary cultures as vector genomes were recruited for transduction (Russell et al., ibid. and Alexander et al., *J Virol.* 68:8282–8287, 1994). In a similar experiment, a time course of increased transduction after drug or radiation treatments was carried out. Briefly, stationary human fibroblast cultures were pretreated overnight with 40 mM hydroxyurea or 3.0 μM etoposide; or immediately prior to infection with 4000 rads of γ-irradiation. As a control, a stationary culture was left untreated. After pretreatment, all cultures were infected with AAV-LAPSN. Cultures were stained for AP expression at the 2, 5, 8, and 12 or 14 days post infection (controls were assayed at 2, 3, 7, and 12 days post infection). The relative transduction efficiency was determined as the number of transductants/ml of vector stock produced at each time point divided by the number in untreated stationary cultures 2 days post-infection. In all cases, the transduction efficiency 12–14 days after infection was higher than 2 days after infection, and, except for hydroxyurea treatment, there was at least a 10-fold increase in the number of transductants. Thus the increased gene expression produced by these agents was stable and often increased further over 12–14 days. The maximum effects observed with etoposide, hydroxyurea, and γ-irradiation were all similar, suggesting that there may be a limit to the increase in transduction that can be achieved.

EXAMPLE 16

Transduction with Therapeutic AAV Vector

A recombinant AAV vector carrying a globin gene is constructed as generally described by Walsh et al., *Proc. Natl. Acad Sci. US.A.* 89, 7257–7261 (1992). Bone marrow is removed using standard bone marrow harvest techniques from a patient suffering from sickle cell anemia or thalassemia. The patient bone marrow is treated with hydroxyurea at concentrations of from 0.40 to 40.00 mM as described above. After preincubation with hydroxyurea for 16 hours, the bone marrow is exposed to the AAV recombinant vector under transducing conditions as described above. After infection the treated bone marrow is reinfused into the patient using standard reinfusion protocols. The patient is monitored for increased globin production using clinical indica of successful treatment of the underlying pathology.

EXAMPLE 17

Increased Transduction of Dividing and Non-Dividing Cells.

The preferential transduction of AAV vectors into the small proportion (2–4%) of S phase cells present in untreated stationary cultures was shown by transducing stationary cultures in the presence of $^3$H-thymidine, staining for AP expression and performing autoradiography. In similar experiments, cultures exposed to $^3$H-thymidine had a 12-fold higher transduction frequency than untreated cultures, and 85% of the transductants had passed through S phase, in agreement with published results. The addition of hydroxyurea, etoposide, or camptothecin further increased transduction frequencies, but combinations of agents did not increase transduction significantly more than the most effective agent alone. Surprisingly, there were large increases in both S phase and non-S phase transductants, and when the decreased number of S phase cells present in the cultures was taken into account, some treatments actually increased the transduction preference for S phase cells. The increase in S phase transductants was higher than expected based on experiments with dividing cultures, suggesting either that $^3$H-thymidine alters the effects of these drugs, or that the S phase cells present in confluent fibroblast cultures respond differently than those in sub-confluent, proliferating cultures.

EXAMPLE 18

Selective Identification of DNA Metabolism Altering Drugs that Enhance Transduction By AAV Vectors Numerous agents that alter DNA metabolism are known in the art. Previous Examples have illustrated that a number of such drugs have the capacity to increase the frequency with which AAV vectors can transduce both stationary and dividing human cells. Because more pronounced effects were observed with stationary cells, stationary cultures are preferred for selectively identifying those DNA metabolism altering compounds which have the capacity to enhance transduction of AAV vectors. However, if desired, dividing cells can be used instead in the following procedure. Various doses of the test compound are applied overnight to cultures of primary human fibroblasts or other cells such as 293 cells. Negative control cultures receive no compound treatment, while positive controls receive 40 mM hydroxyurea or 3 μM etoposide. After the test compound is washed from the cell, the cells are infected with AAV-LAPSN. After a 48 hour incubation, AP production or G418 resistance are assayed as described above. Enhancement of transduction is determined by comparing assay results or other indicia of transduction in the treated and untreated cultures. The efficacy of the test compound as a transduction enhancer is determined by comparing the enhancement obtained using the test compound with the enhancement obtained using the compound chosen as a positive control.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A method of increasing adeno-associated virus vector transduction of a cell comprising the steps of:
   a. treating a cell with an effective level of an agent that alters DNA metabolism in a cell; and
   b. exposing the cell to a recombinant adeno-associated virus vector for a period of time for transduction of the cell by the vector.

2. A method according to claim 1 wherein the agent is selected from the group consisting of agents that alter the DNA structure within the cell, agents that alter DNA repair within the cell, agents that alter DNA synthesis, and agents that alter the chromosome integrity within the cell.

3. A method according to claim 2 wherein the agent that alters the DNA structure within the cell is selected from the group consisting of agents that damage the cellular DNA, agents that cause dimerization of adjacent nucleotides, agents that cause scission of the DNA backbone of at least one strand of the DNA, and agents that alkylate DNA.

4. A method according to claim 2 wherein the agent is selected from the group consisting of tritiated thymidine, UV irradiation, gamma irradiation, cis-platinum, etoposide, hydroxyurea, aphidocolin, and camptothecin.

5. A method according to claim 1 wherein the cell is a non-dividing cell.

6. A method of claim 1 wherein the cell is exposed to the recombinant adeno-associated virus vector in vitro.

7. A method of claim 1 wherein the cell is exposed to the recombinant adeno-associated virus vector ex vivo.

8. A method of claim 1 wherein the cell is exposed to the recombinant adeno-associated virus vector in vivo.

9. A method of screening for an agent capable of increasing transduction of a cell population with a recombinant adeno-associated virus vector, comprising the steps of:

a. treating a cell population with an effective level of a test agent, wherein the test agent alters DNA metabolism in a cell;
b. exposing the treated cell population and an untreated cell population with a recombinant adeno-associated virus vector;
c. incubating the adeno-associated virus vector with the cell populations to allow transduction of each cell population;
d. assaying the levels of transduction of the treated and untreated cell populations; and
e. determining that the test agent is capable of increasing transduction of the cell population if the level of transduction of the treated cell population is greater than the level of transduction of the untreated cell population.

* * * * *